(12) United States Patent
Fischell et al.

(10) Patent No.: US 8,262,625 B1
(45) Date of Patent: Sep. 11, 2012

(54) INTRODUCER SHEATH HAVING A HEMOSTASIS VALVE WITH AN ADHESIVE MEANS FOR ATTACHMENT TO THE SKIN

(75) Inventors: Robert E. Fischell, Dayton, MD (US); Scott J. S. Fischell, Hardy, VA (US)

(73) Assignee: Fischell Innovations, LLC, Fairhaven, NJ (US)

( * ) Notice: Subject to any disclaimer, the term of this patent is extended or adjusted under 35 U.S.C. 154(b) by 0 days.

(21) Appl. No.: 13/105,043

(22) Filed: May 11, 2011

(51) Int. Cl.
*A61M 5/32* (2006.01)
*A61M 5/178* (2006.01)

(52) U.S. Cl. .................................. 604/174; 604/167.01
(58) Field of Classification Search .................. 604/171, 604/173–180, 164.01, 164.02, 165.01, 165.04, 604/167.01, 167.03, 167.05
See application file for complete search history.

(56) References Cited

U.S. PATENT DOCUMENTS

| 5,827,230 | A | 10/1998 | Bierman |
| 5,827,239 | A | 10/1998 | Dillon et al. |
| 5,944,697 | A * | 8/1999 | Biche ............................ 604/174 |
| 6,863,674 | B2 * | 3/2005 | Kasahara et al. ............. 606/108 |
| 2007/0066958 | A1 * | 3/2007 | Wright .......................... 604/500 |
| 2009/0054845 | A1 * | 2/2009 | Puhasmagi et al. ........... 604/180 |

* cited by examiner

*Primary Examiner* — Kevin C Sirmons
*Assistant Examiner* — Andrew Gilbert
(74) *Attorney, Agent, or Firm* — Stoel Rives, LLP

(57) ABSTRACT

An introducer sheath for placement of a tubular shaft into the vascular system of a human subject. The introducer sheath has a tubular shaft, a side arm, and a hemostasis valve placed at a proximal portion of the introducer sheath. The hemostasis valve has an adhesive pad formed integral with the shell of the hemostasis valve. The adhesive pad is designed to attach and detach a proximal section of the introducer sheath to and from the skin of the human subject.

4 Claims, 2 Drawing Sheets

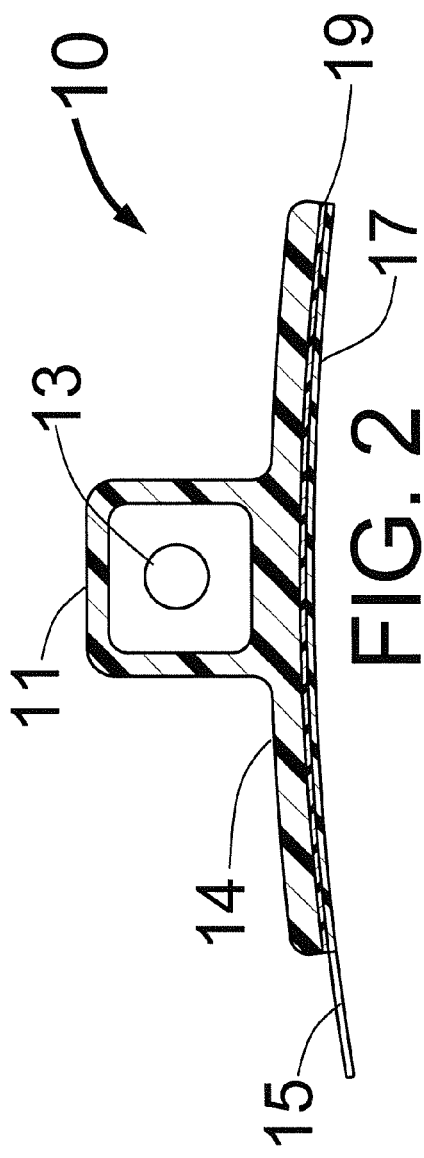
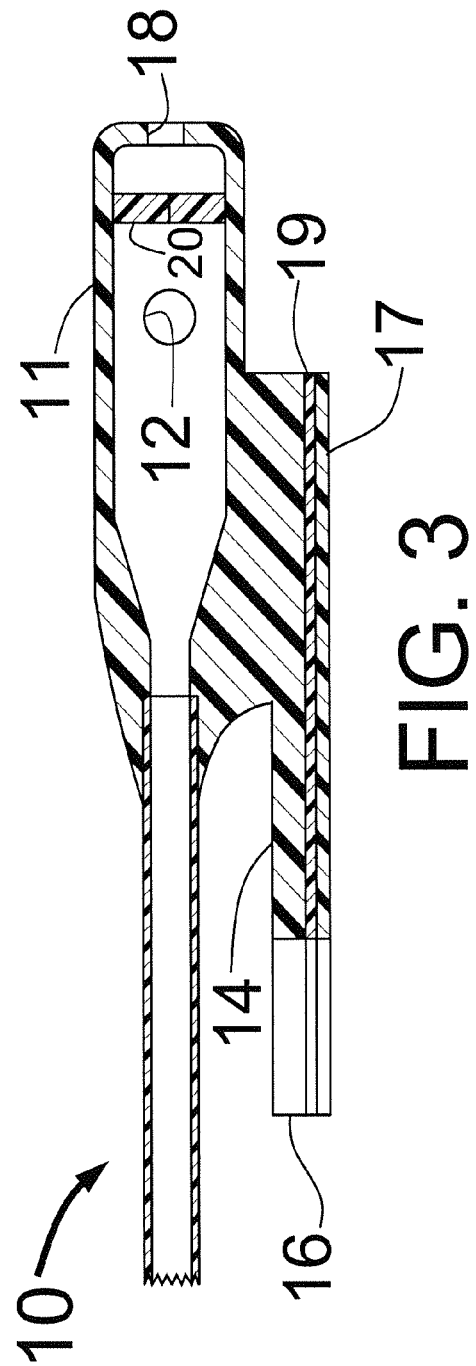

INTRODUCER SHEATH HAVING A HEMOSTASIS VALVE WITH AN ADHESIVE MEANS FOR ATTACHMENT TO THE SKIN

FIELD OF USE

This invention is in the field of devices to assist in the placement of catheters through the skin to treat certain coronary and peripheral vascular disorders.

BACKGROUND OF THE INVENTION

At the present time, physicians place an introducer sheath through the skin of a patient to access that patient's vascular system. Two usual places to gain access are through the skin at the groin to enter the femoral artery and through the skin in the wrist to access the radial artery. After the introducer sheath is placed through the skin, the physician will typically use a suture to fasten the proximal end of the introducer sheath to the patient's skin. That process requires the opening of an additional package that contains the suture thread and a needle, and also requires skin penetration that can be somewhat painful for the patient and has the possibility of infection.

In U.S. Pat. No. 5,827,239, S. F. Bierman has shown an adhesive attachment to the skin onto which certain catheters could be connected. One disadvantage of Bierman's attachment means is that it requires a separate sterile package to be opened in addition to the sterile package containing the introducer sheath. This requires additional procedure time and the separate sterilization of two different packages which increase costs. Another disadvantage of the Bierman device is that it is not as secure a holding means for a hemostasis valve as would be achieved if the adhesive attachment means was formed integral as one piece with the shell of the hemostasis valve of the introducer sheath. A highly reliable and rapid attachment means to secure the proximal end of the introducer sheath to the patient's skin would be an important improvement in the design of introducer sheaths.

SUMMARY OF THE INVENTION

A key feature of the present invention is a novel attachment means located at a proximal section of the sheath. This attachment means is designed to facilitate rapid attachment and detachment of the proximal end of the sheath to the patient's skin. One embodiment of the present invention is an introducer sheath that is improved by having an adhesive pad located at or near the sheath's proximal end that detachably attaches the introducer sheath to the patient's skin without requiring any additional parts that come from a separate sterile package such as a needle and a suture or a separate adhesive pad. Specifically, one embodiment of the present invention is a flexible adhesive pad that is formed integral as one piece with the shell of the hemostasis valve that is situated at the sheath's proximal end. The adhesive pad has a pressure sensitive adhesive on one side that is covered by a removable plastic cover sheet which is removed to expose the pressure sensitive adhesive surface of the adhesive pad in order to attach the introducer sheath to the skin. Either before or after the shaft of the introducer sheath is placed through the skin, the thin plastic (or paper) cover sheet that covers the pressure sensitive adhesive is removed. When the introducer sheath is then advanced into the target blood vessel to its fully inserted position, and the plastic cover sheet of the adhesive pad has been removed, the pressure sensitive adhesive pad is pushed firmly against the skin thereby firmly attaching the sheath to the patient's skin without requiring a sutured connection.

The use of a suture is now the conventional means that is used to make the attachment of the proximal end of an introducer sheath to the skin. The present invention eliminates the extra time required to open a separate package containing the needle and suture material, and the time required to place the suture through the introducer sheath and into the skin. The present invention also eliminates the penetration of the skin that can be somewhat uncomfortable for the patient and increases the possibility of infection. Still further, the cost of the needle and suture in a sterile pack is avoided. It is believed that suturing for retention of the sheath requires about 2 minutes of time for the operator. As a comparison, removing a plastic sheet cover from a pressure sensitive adhesive attachment to the sheath's proximal end and pushing the pressure sensitive adhesive against the skin could probably be accomplished in only 2-3 seconds. Furthermore, removing the suture could again take about 2 minutes compared to removing the pressure sensitive adhesive pad that would probably take less than 2 seconds to accomplish. Such time saving and ease of use is appreciated by those physicians who perform this procedure.

If a separate adhesive pad is used to attach an introducer sheath to the patient's skin, this requires the time to open an additional sterile package and to place it in the proper position on the skin before the introducer sheath is placed with its shaft into the patient's vascular system. The most accurate position for the introducer sheath is not guaranteed as is the case when the adhesive pad is formed integral with the hemostasis valve. Also, using a separate adhesive pad there is always the possibility that the hemostasis valve will slip off of the pad when there is a considerable force exerted on the separate pad when a catheter is pushed into or pulled out of the hemostasis valve. Thus there are many advantages to having a flexible adhesive pad that is formed integral as part of the hemostasis valve which hemostasis valve is part of the introducer sheath.

Thus one object of the present invention is to provide a means to secure the proximal end of an introducer sheath to a patient's skin without the use of a suture or a separate adhesive pad, this means being a flexible adhesive pad that is formed integral, as one piece, with the shell of the hemostasis valve that is located at a proximal region of the introducer sheath.

Another object of this invention is to secure the proximal end of an introducer sheath to the skin without using a needle and suture so as to eliminate the discomfort that may be felt by the patient when a needle is used to penetrate his or her skin.

Still another object of this invention is to have a sufficient length of the hemostasis valve lying proximal to the proximal end of the adhesive pad so that it is easily gripped by the doctor who inserts the introducer sheath into the patient's vascular system.

Still another object of this invention is to have a separate distal portion of a hemostasis valve that is free to rotate about a proximal portion of the hemostasis valve, the distal portion including an adhesive pad that is formed integral with the shell of that distal portion of the hemostasis valve.

These and other objects and advantages of this invention will become obvious to a person of ordinary skill in this art upon reading the detailed description of this invention including the associated drawings as presented herein.

BRIEF DESCRIPTION OF THE DRAWINGS

FIG. 2 is a cross section at "A-A" of FIG. 1 showing the construction of the adhesive pad and the hemostasis valve.

FIG. 3 is a cross section at "B-B" of FIG. 1 showing the construction of the adhesive pad and the hemostasis valve.

DETAILED DESCRIPTION OF THE INVENTION

Figure 1:
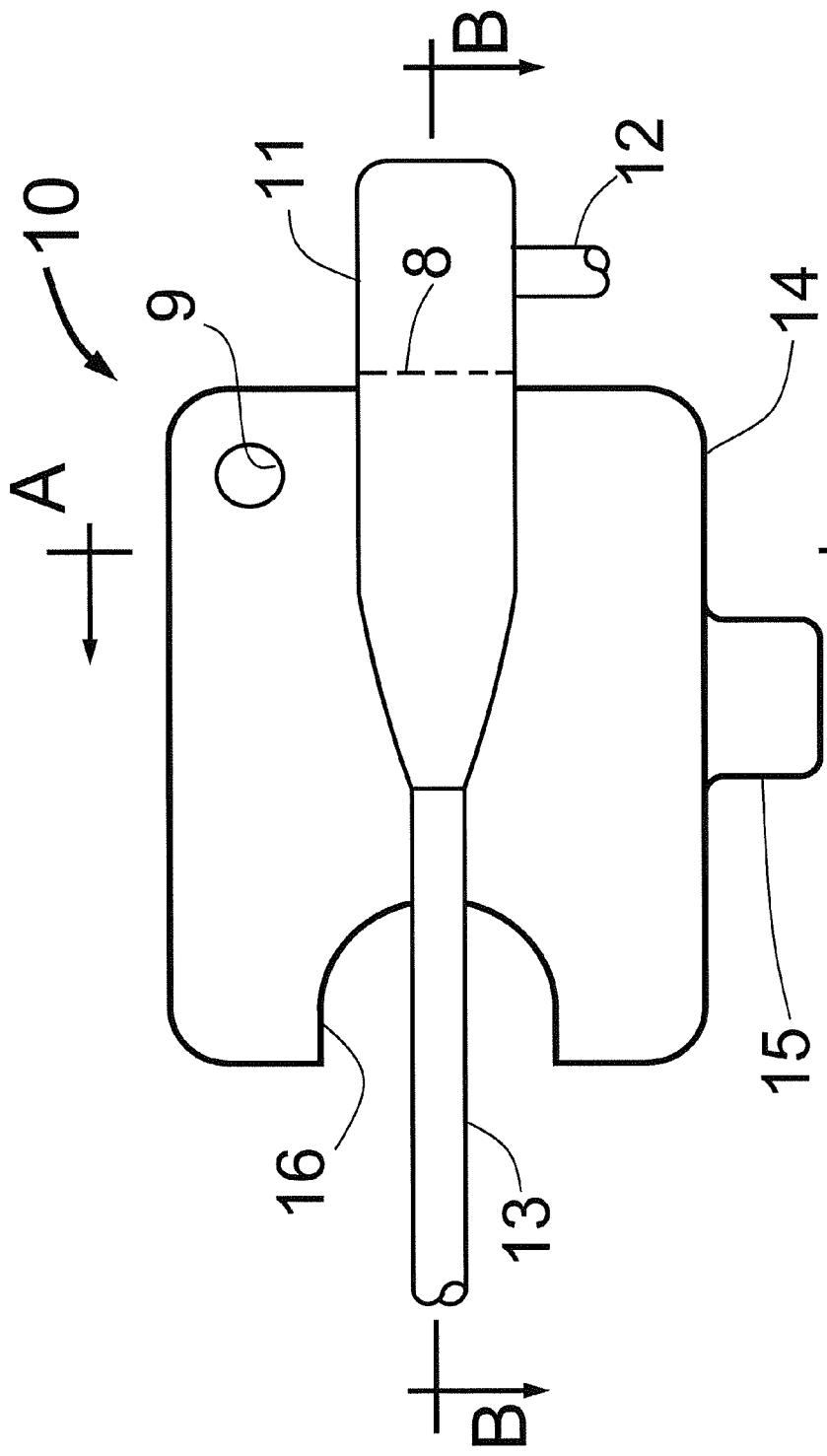
FIG. 1 is a top view of a preferred embodiment of the present invention wherein the adhesive pad is attached to the bottom surface of the hemostasis valve.

FIG. 1 is a top view of the present invention showing a proximal portion of an introducer sheath 10 that has a hemostasis valve 11 located at the sheath's proximal end. The hemostasis valve 11 has a side tubing 12 that is used to flush the sheath with normal saline solution and to inject various medications as needed to treat the patient. At the distal end of the hemostasis valve 11 is the shaft 13 that is placed into the patient's vascular system for introducing various catheters. Formed integral with the shell of the hemostasis valve 11 is a flexible pad 14 onto which is formed a thin layer of pressure sensitive adhesive 19 as shown in FIGS. 2 and 3. A tab 15 is used to remove a thin plastic covering 17 from the adhesive layer 19 immediately before the flexible pad 14 is pushed against the skin to secure the introducer sheath 10 to the patient's skin. Also shown in FIG. 1 is a suture hole 9 that can be used by the interventional cardiologist to place a suture through the flexible pad 14 if it is decided to increase the holding power of the pad 14 onto the patient's skin.

One important feature of this invention is the opening 16 that is made at the distal end of the pad 14 to allow easy passage of the shaft 13 into and through the patient's skin. This opening allows the passage of the shaft 13 into the patient's skin at a place that is much closer to the hemostasis valve 11 which is a desirable attribute of this introducer sheath 10. A second important feature of this invention is the juxtaposition of the hemostasis valve 11 and the pad 14. Specifically, a reasonable length of the hemostasis valve 11 is situated proximal to the proximal end of the pad 14 so that it can be easily grasped by the interventional cardiologist for readily inserting the shaft 13 through the patient's skin.

FIG. 2 is a cross section of the introducer sheath 10 at section A-A of FIG. 1 showing the hemostasis valve 11, the interior lumen of the shaft 13, the flexible pad 14 onto which is attached the adhesive 19 covered by the removable plastic sheet 17. The tab 15 is used to remove the plastic sheet 17 from the adhesive layer 19 immediately prior to having the interventional cardiologist push the pad 14 against the patient's skin to secure the proximal portion of the introducer sheath 10 to the patient's skin. When the time has come to remove the adhesive pad 14 from the patient's skin, the operator can pull on the proximal portion of the hemostasis valve 11 to accomplish that removal. A separate tab to pull the adhesive pad 14 off of the patient's skin could be used but that is not really required.

FIG. 3 is a cross section of the introducer sheath 10 at section B-B of FIG. 1. This cross section clearly shows that the pad 14 is formed integral, as one piece, with the shell of the hemostasis valve 11. FIG. 3 also shows the interior lumen of the tubing 12, the shaft 13 and the flexible pad 14 that has a layer of pressure sensitive adhesive 19 covered by a removable plastic sheet 17. FIG. 3 also shows the entry port 18 in the shell of the hemostasis valve 11 and the diaphragm 20 whose function is to eliminate outward blood flow through the port 18 whether or not a catheter (not shown) is placed through the hemostasis valve 11.

Although the hemostasis valve 11 to which the adhesive pad is attached is shown in FIGS. 1, 2 and 3 to be formed from a single piece of a plastic material, one embodiment of this invention envisions that the distal portion of the hemostasis valve 11 to which the adhesive pad 14 is attached could be designed to rotate about a proximal portion of the hemostasis valve 11. The dotted line 8 in FIG. 1 represents the line of separation between a distal portion of the hemostasis valve 11 that can rotate freely about a proximal portion of the hemostasis valve 11. It is envisioned that the proximal portion of the hemostasis valve 11 should be at least 1.0 cm in length so that it can be readily gripped by the interventional cardiologist to insert the introducer sheath through the patient's skin. This proximal portion should extend for at least 1.0 cm for easy gripping for insertion whether or not the distal portion of the hemostasis valve 11 is free to rotate about that proximal portion of the hemostasis valve 11.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. An introducer sheath for placement of a tubular shaft into the vascular system of a human subject, the introducer sheath having a tubular shaft, a side arm and a shell of a hemostasis valve placed at a proximal portion of the introducer sheath, the shell of the hemostasis valve having an adhesive pad formed integral with the shell of the hemostasis valve, the adhesive pad being designed to readily attach and detach a proximal section of the introducer sheath to and from the skin of the human subject, the adhesive pad having an adhesive plane substantially parallel to a longitudinal axis of the shell of the hemostasis valve, the shell of the hemostasis valve having a distal portion to which the adhesive pad is attached, the shell of the hemostasis valve having a proximal portion which is at least one centimeter long and is free to rotate about the distal portion of the shell of the hemostasis valve, the adhesive pad having an extended base member that extends in a distal direction past the shell of the hemostasis valve, the tubular shaft of the introducer sheath extending in a distal direction, and the tubular shaft spaced apart from the base member.

2. The introducer sheath of claim 1 where the adhesive pad is attached to a bottom surface of the shell of the hemostasis valve of the introducer sheath.

3. An introducer sheath for placement of a tubular shaft into the vascular system of a human subject, the introducer sheath having a tubular shaft, a side arm and a shell of a hemostasis valve placed at a proximal portion of the introducer sheath, the shell of the hemostasis valve having an adhesive pad formed integral with the shell of the hemostasis valve, the adhesive pad being designed to readily attach and detach a proximal section of the introducer sheath to and from the skin of the human subject, the adhesive pad having an adhesive plane substantially parallel to a longitudinal axis of the shell of the hemostasis valve, the shell of the hemostasis valve being attached to the adhesive pad, the adhesive pad having an extended base member that extends in a distal direction past the shell of the hemostasis valve, the tubular shaft of the introducer sheath extending in a distal direction, and the tubular shaft spaced apart from the base member, wherein a proximal portion of the shell of the hemostasis valve lies at least one centimeter proximal to the proximal end of the adhesive pad so that this proximal portion of the shell of the hemostasis valve can be held by a practitioner for placement of the introducer sheath into the patient's vascular system.

4. An introducer sheath for placement of a tubular shaft into the vascular system of a human subject, the introducer sheath having a tubular shaft, a side arm, a diaphragm and a shell of a hemostasis valve placed at a proximal portion of the introducer sheath, the shell of the hemostasis valve having an adhesive pad formed integral with the shell of the hemostasis valve, the adhesive pad being designed to readily attach and detach a proximal section of the introducer sheath to and from the skin of the human subject, the adhesive pad having an adhesive plane substantially parallel to a longitudinal axis of the shell of the hemostasis valve, the shell of the hemostasis valve being attached to the adhesive pad, the adhesive pad having an extended base member that extends in a distal direction past the shell of the hemostasis valve, the tubular shaft of the introducer sheath extending in a distal direction, the tubular shaft spaced apart from the base member, and the diaphragm being located proximal a proximal end of the adhesive pad.

* * * * *